United States Patent [19]

Lloyd et al.

[11] Patent Number: 5,374,241
[45] Date of Patent: Dec. 20, 1994

[54] ELECTRODES FOR IONTOPHORESIS

[75] Inventors: Lindsay B. Lloyd, West Jordan; Jon E. Beck; Tomasz J. Petelenz, both of Salt Lake City; Clay H. Holt, Riverton; William F. Felman, West Valley City, all of Utah

[73] Assignee: Iomed, Inc., Salt Lake City, Utah

[21] Appl. No.: 45,040

[22] Filed: Apr. 7, 1993

Related U.S. Application Data

[63] Continuation-in-part of Ser. No. 645,028, Jan. 23, 1991, abandoned, which is a continuation-in-part of Ser. No. 383,939, Jul. 21, 1989, Pat. No. 5,087,242.

[51] Int. Cl.$^5$ .............................................. A61N 1/30
[52] U.S. Cl. .................................. 604/20; 607/149; 607/153
[58] Field of Search .................. 604/20; 607/149–153

[56] References Cited

U.S. PATENT DOCUMENTS

| | | | |
|---|---|---|---|
| 4,033,334 | 7/1977 | Fletcher et al. | 128/2.1 |
| 4,164,226 | 8/1979 | Tapper | 128/419 |
| 4,327,728 | 5/1982 | Elias | 128/285 |
| 4,383,529 | 5/1983 | Webster | 604/20 |
| 4,416,274 | 11/1983 | Jacobsen et al. | 604/20 |
| 4,419,092 | 12/1983 | Jacobsen et al. | 604/20 |
| 4,474,570 | 10/1984 | Ariura et al. | 604/20 |
| 4,702,732 | 10/1987 | Powers et al. | 604/20 |
| 4,708,149 | 11/1987 | Axelgaard et al. | 128/798 |
| 4,722,726 | 2/1988 | Sanderson et al. | 604/20 |
| 4,731,049 | 3/1988 | Parsi | 604/20 |
| 4,731,926 | 3/1988 | Sibalis | 29/877 |
| 4,747,819 | 5/1988 | Phipps et al. | 604/20 |
| 4,842,577 | 6/1989 | Konno et al. | 604/20 |
| 4,878,892 | 11/1989 | Sibalis et al. | 604/20 |
| 4,921,475 | 5/1990 | Sibalis | 604/20 |
| 4,989,607 | 2/1991 | Keusch et al. | 128/640 |
| 5,002,814 | 3/1991 | Knack et al. | 428/85 |
| 5,084,006 | 1/1992 | Lew et al. | 604/20 |
| 5,087,241 | 2/1992 | Mathiesen et al. | 604/20 |
| 5,087,242 | 2/1992 | Petelenz | 604/20 |
| 5,147,297 | 9/1992 | Myers et al. | 604/20 |
| 5,156,591 | 10/1992 | Gross et al. | 604/20 |
| 5,158,537 | 10/1992 | Haak et al. | 604/20 |
| 5,203,768 | 4/1993 | Haak et al. | 604/20 |
| 5,236,412 | 8/1993 | Lloyd et al. | 604/20 |

FOREIGN PATENT DOCUMENTS

| | | | |
|---|---|---|---|
| 0058920 | 9/1982 | European Pat. Off. | 20/604 |
| 0299615 | 1/1989 | European Pat. Off. | 20/604 |
| 2184016 | 6/1987 | United Kingdom | 20/604 |
| 91/1215 | 8/1991 | WIPO | 30/1 |
| 91/11216 | 8/1991 | WIPO | 30/1 |
| 9115260 | 10/1991 | WIPO | 604/20 |
| 9207618 | 5/1992 | WIPO | 604/20 |
| 9207619 | 5/1992 | WIPO | 604/20 |
| 9210235 | 6/1992 | WIPO | 604/20 |

*Primary Examiner*—C. Fred Rosenbaum
*Assistant Examiner*—Ronald K. Stright, Jr.
*Attorney, Agent, or Firm*—Workman, Nydegger & Seeley

[57] ABSTRACT

An improved electrode is disclosed for use in administering drug by means of iontophoresis, comprising a conductive element for receiving an electric current from a current source; a reticulated element having a plurality of reticulum for receiving an ionic drug solution for iontophoretic delivery, the reticulum being loaded or having applied thereto a hydrophilic polymer which is viscous when hydrated; and means for securing the reticulated element to the conductive element so that electric current will be distributed substantially uniformly through the reticulated element when hydrated and when current is delivered to the conductive element. The presently preferred embodiment utilizes open cell polyurethane foam as the reticulated element and high molecular weight polyethylene oxide as the hydrophilic polymer. The reticulum is further loaded with Tween 20, a surfactant, which serves to improve the rate of hydration. A reticulated element formed in accordance with the present invention is pliable and conformable both when in wet or dry state, making an electrode formed in accordance with the present invention susceptible of a wide variety of shapes and sizes and relatively easy to manufacture at reasonably low cost.

12 Claims, 3 Drawing Sheets

ELECTRODES FOR IONTOPHORESIS

CONTINUING APPLICATION DATA

The present application is a continuation-in-part application of pending U.S. application Ser. No. 07/645,028, filed Jan. 23, 1991 now abandoned, entitled "Hydratable Bioelectrode", which is a continuation-in-part of U.S. Pat. No. 5,087,242, Ser. No. 383,939, filed Jul. 21, 1989 and issued Feb. 11, 1992.

BACKGROUND OF THE INVENTION

1. Technical Field

The present invention relates to iontophoretic electrodes, with particular emphasis on electrodes which are used to administer a drug by means of iontophoresis. Although the preferred embodiment is directed to an electrode packaged in dry form which is to be hydrated immediately prior to use, it is also possible to utilize the apparatus of the invention in connection with electrodes provided in a hydrated form.

2. Background Information

Iontophoresis is a method for delivering an ionic form of a drug through the skin in the presence of an electrical potential. It is typically performed by placing an electrode containing an ionic drug solution in contact with the skin at the location where drug is to be transported. A second electrode is placed on the skin near the first electrode, and voltage is applied sufficient to cause current to pass through the skin, thereby completing the electrical circuit between the electrodes. As current flows, the ionic drug molecules migrate through the skin under the influence of the second electrode. One advantage of iontophoresis is that it is a noninvasive means of administering drug, yet avoids many problems which are encountered in oral administration of drugs.

One of the most common uses of iontophoresis is to administer dexamethasone sodium phosphate for the local treatment of local inflammation, tendinitis, bursitis, arthritis, or carpal tunnel syndrome. Iontophoresis is also frequently used to administer lidocaine hydrochloride to serve as a local anesthetic.

In view of the significant clinical benefits of iontophoretic administration of drugs, much attention has been given to the use of iontophoresis as a method for administering other drugs, and it is anticipated that iontophoresis will develop as a method of choice in an increasing number of applications.

One general class of electrode designs involves the use of a conductive element associated with a compartment or pouch into which a drug solution is introduced. One wall of the pouch typically comprises a permeable barrier, which serves to contain the solution, but permits drug ions to pass therethrough. Examples of such electrodes can be seen in U.S. Pat. Nos. 4,250,878; 4,419,092; and 4,477,971.

Pouch-type designs suffer from several problems. For example, the use of a permeable barrier inhibits thorough and complete wetting of the skin lying thereunder, which results in areas of relatively high electrical resistance. The diffusion rate through the permeable membrane also has an undesirable inhibiting effect upon the rate of drug delivery in comparison to an electrode design wherein the drug is directly against the skin.

Another problem with the pouch designs is the need to guard against leakage of the drug solution from the pouch during use. This requires use of a sealed means for introducing drug solution into the pouch, which increases the cost of this type of electrode.

Pouch designs also suffer from a lack of conformability. This exacerbates the problem of uneven wetting of the skin and results in uneven delivery of drug. Lack of conformability also increases the incidence of skin irritation and burns during iontophoresis because it results in an uneven application of electrical current.

A second class of electrode designs involve the use of a conductive element associated with a gel material for containing ionized drug without the use of a pouch. Examples of such bioelectrodes are found in U.S. Pat. Nos. 4,383,529; 4,474,570; and 4,747,819. Typically, these gel-type electrodes incorporate ionized drug into the gel at the time of manufacture. This makes storage and shipping of the electrode more difficult, and shortens the shelf-life of the electrode because it must be used prior to unacceptable degradation of the drug. Attempts to hydrate the gels at the time of use were generally unsuccessful due to the long time required to obtain uniform hydration. Use prior to full and complete hydration leads to uneven current distribution which, as noted above, can result in skin inflammation or burns. As with pouch designs, the use of gel-type electrodes also fails to completely wet the skin lying thereunder resulting in the problems already discussed.

A third class of electrode design is disclosed in copending U.S. application Ser. No. 07/645,028, filed Jan. 23, 1991, entitled "Hydratable Bioelectrode", and U.S. Pat. No. 5,087,242, filed Jul. 21, 1989 and issued Feb. 11, 1992. The text of said copending application and issued patent is hereby incorporated by reference. This third type of electrode design generally utilizes a conductive element associated with a hydratable element. As described in the copending application and the issued patent, the hydratable element is typically formed of a stack of sheets of a dry crosslinked hydrogel, such as crosslinked polyethylene oxide (PEO).

Although a vast improvement over pouch designs and gel-type designs, the crosslinked hydrogel electrode designs still suffer from several significant disadvantages. For example, the dimensions of a hydratable element utilizing a crosslinked hydrogel design are limited because of the requirement for liquid to penetrate from the edges of adjacent sheets to the center thereof before hydration causes blocking; dimensions in excess of about 5 centimeters have been found to result in imperfect hydration, probably due to collapse of the hydrogel sheets upon hydration, thereby blocking further hydration interior of the blockage. Also, in dry form, the stack of sheets of crosslinked hydrogel is relatively stiff and essentially planar. Both of these factors place limitations upon the size, shape, and uses of the electrode.

Also, some manufacturing problems are encountered when preparing the stack of crosslinked hydrogel sheets. For example, the requirement to bind the stack of sheets together adds manufacturing steps and costs. Additionally, since the sides of adjacent sheets must remain open to entry of liquid at the time of hydration, limitations are placed upon the manner in which the hydratable element may be affixed to the conductive element.

SUMMARY OF THE INVENTION

From the foregoing, it will be appreciated that it is a primary object of the present invention to provide an electrode design which is capable of rapid and uniform hydration.

Another object of the present invention is to provide an electrode design which is conformable to the contours of tissue into which a drug is to be administered.

Yet another object of the present invention is to provide an electrode design which is susceptible to alterations in size and shape to meet the needs of specific applications.

A further object of the present invention is to provide an electrode design which wets the skin so as to improve efficiency and minimize electrode-induced unequal current distribution at different skin locations.

Yet another object of the present invention is to provide electrode designs which are relatively easy to manufacture at reasonably low cost.

Additional objects and advantages of the invention are set forth hereinbelow in the detailed description, or will be appreciated by the practice of the invention.

To achieve the foregoing objects, and in accordance with the invention as embodied and broadly described herein, an improved electrode for use in administering drug by means of iontophoresis advantageously comprises a conductive element for receiving an electric current from a current source; a reticulated element having a plurality of reticulum for receiving an ionic drug solution for iontophoretic delivery, the reticulum being loaded or having applied thereto a hydrophilic polymer which is viscous when hydrated; and means for securing the reticulated element to the conductive element so that electric current will be distributed substantially uniformly through the reticulated element when hydrated and when current is delivered to the conductive element. The improved electrode of the present invention could also be used as the second, non-drug electrode, of an iontophoresis application.

The presently preferred embodiment utilizes open cell polyurethane foam as the reticulated element and high molecular weight polyethylene oxide as the hydrophilic polymer, and further includes Tween 20, a surfactant, loaded in the reticulum in order to improve the rate of hydration. A reticulated element formed with these materials is pliable and conformable both when in wet or dry state, making an electrode formed in accordance with the present invention susceptible of a wide variety of shapes and sizes.

BRIEF DESCRIPTION OF THE DRAWINGS

In the accompanying drawings, which represent the best mode presently contemplated for carrying out the present invention.

DETAILED DESCRIPTION OF THE PREFERRED EMBODIMENTS

The present invention is directed to improved electrodes primarily for use in delivering drugs by means of iontophoresis. Such improved iontophoretic electrodes have a conductive element for receiving an electric current from a conventional iontophoretic electric current source and a reticulated element having a plurality of reticulum containing a hydrophilic polymer to serve as a reservoir of drug for delivery. Means are also provided for securing the reticulated element to the conductive element so that electric current will be distributed substantially uniformly through the reticulated element when current is delivered.

As used herein, the term "reticulated" means that the reticulated element contains a network of fibers or other structure which results in a three-dimensional porous configuration. The term "reticulum" is used to refer to regions involving individual pores and associated fibers or other structure. A plurality of reticulum form the reticulated element.

The Apparatus of the Present Invention

Figure 1:
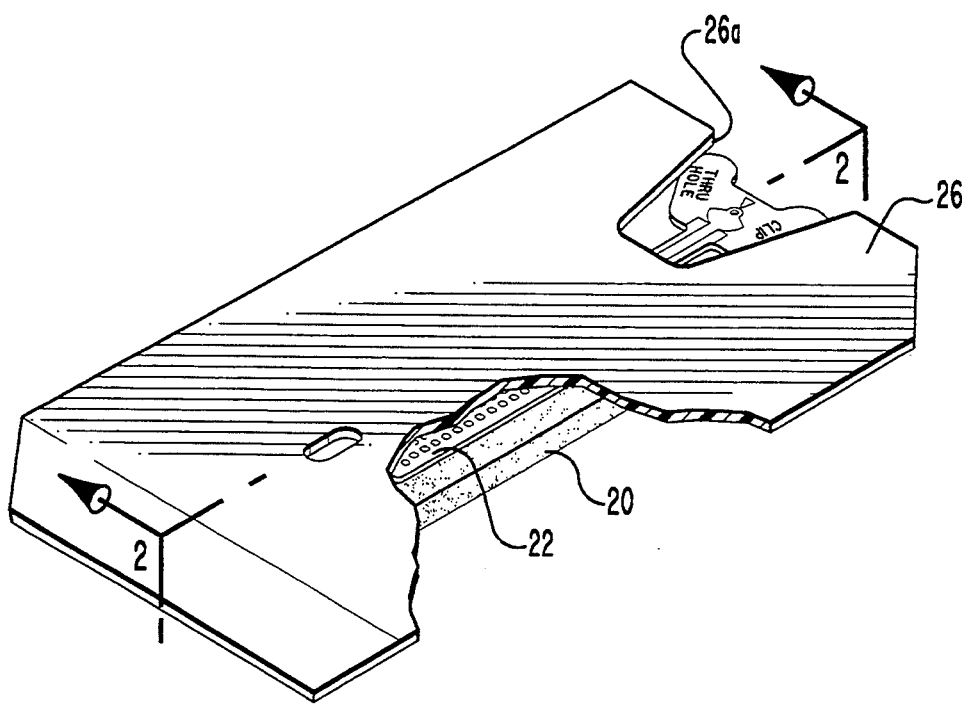
FIG. 1 is a perspective view of a presently preferred electrode in accordance with the present invention.
Figure 2:
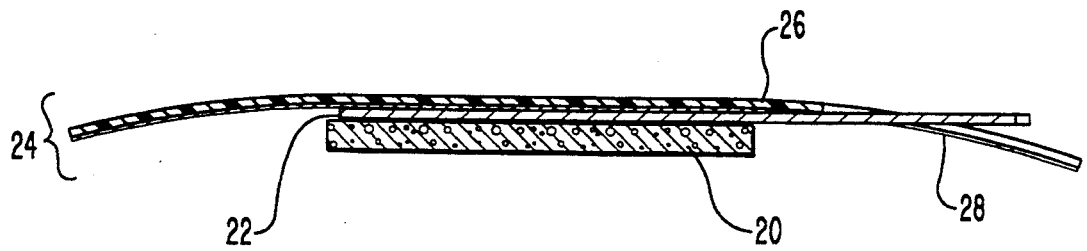
FIG. 2 is a cross sectional view taken along the line 2—2 of FIG. 1.

FIGS. 1 and 2 illustrate a presently preferred form of an electrode in accordance with the present invention which is useful in typical iontophoretic applications. There, an elongated planar reticulated element 20 is illustrated as being in intimate contact with a substantially coextensive conductive element 22, although the edges of the conductive element preferably terminate short of the edges of the reticulated element (See FIG. 1) so as to reduce the likelihood that the conductive element can come in direct contact with the skin during use.

Figure 4:
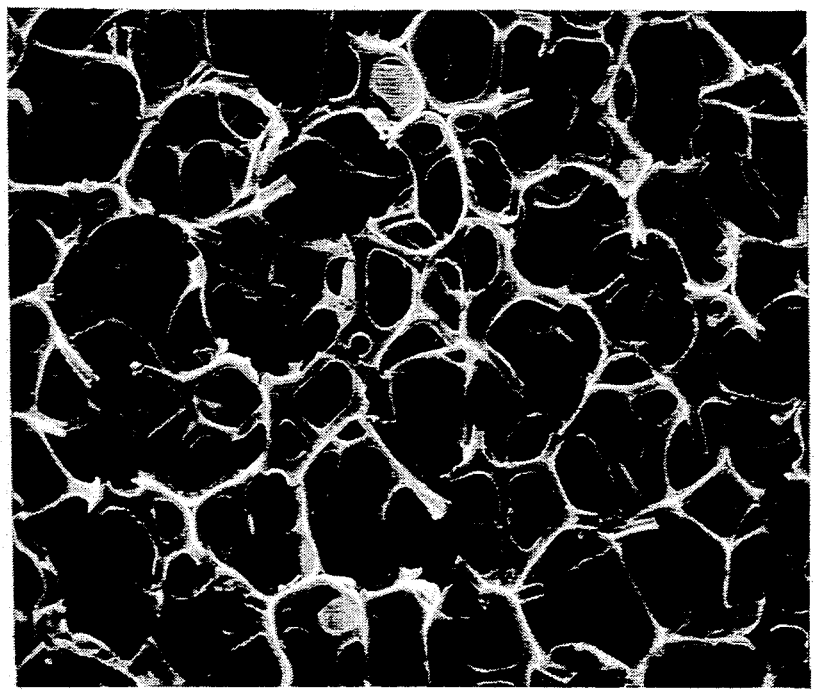
FIG. 4 is photograph taken through a scanning electron microscope showing a typical reticulated element useful in the practice of the present invention.

Various reticulated materials could be used to construct the reticulated element, such as polyurethane foam, PVA foam, Hypol foam, or fibrous mats or fabrics, such as matted rayon. A particularly preferred material, is open cell polyurethane foam having about one hundred pores per linear inch (100 ppi). Such materials are commercially available from various sources, such as that sold under the designation SIFZ Felted foam #2 obtainable from Foamex, Inc., and Crest Felted S-90Z, firmness 2 polyurethane foam distributed by Great Western. FIG. 4 is a 40× photomicrograph taken of a sample of Crest felted S-90Z polyurethane foam taken by a scanning electron microscope at 15 KV. Other useful materials which have been found suitable for use as a reticulated element in the practice of the present invention microcellular hydrophilic polyurethane manufactured by Time Release Science and distributed by Truly Magic Products Inc.; PVA foam E-1 or E-2 distributed by Rippey Corp.; Hypol foam (2002, 2000, or 3000) produced by Hampshire Chemical Inc.; Acquell and hydrophilic foam manufactured by Foamex Foam Inc.

In connection with the consideration of a particular material for possible use as a reticulated element, several preferences may be noted: a reticulated element should be nonirritating, nontoxic and be free of extractable irritants and toxins; should have a relatively consistent pore size; should be relatively soft and conformable, with generally consistent thickness and density (few ripples, knots or waves); and few aqueous ionic moieties associated therewith. Other specific attributes of a material suitable for use as a reticulated element will be more fully appreciated from additional discussion set forth below. Although it will be appreciated that various reticulated materials would be suitable for use, for purposes of brevity, further discussion shall primarily be directed to the use of open cell polyurethane foam as the reticulated element.

It has been found that reticulated material, such as open cell polyurethane, is not suitable for use as a reservoir for an ionic drug solution in its normal condition. It has been discovered that it can be made suitable, however, for use as a reticulated element in accordance with the present invention by loading or applying a suitable hydrophilic material to the reticulum. The presently preferred choice of such a hydrophilic material is high molecular weight polyethylene oxide (PEO), such as Polyox NF coagulant grade made by Union Carbide. For purposes of simplicity and brevity, the following discussion shall primarily discuss the use of PEO in the preparation of the reticulated element, although it should be understood that the discussion nevertheless can be applied to the use of alternative hydrophilic materials, such as high molecular weight polyvinyl alcohol, PVA, poly-N-vinyl pyrrolidone or other substituted pyrrolidones, PVP, polyacrylamides such as poly-N-isopropyl acrylamide, PAAm, NIPPAm, polyhydroxyethyl methacrylate, PHEMA or hydrophilic substituted HEMAs, polysaccharides such as agarose, hydroxy cellulose, HEC, hydroxyethyl methyl cellulose, HPMC, hydroxypropyl cellulose, carboxyethyl cellulose, HPC, hydroxypropyl methyl cellulose, dextrans, modified starches, modified collagens, xanthan gum, modified natural gums, partially neutralized polyelectrolytes such as polyacrylic acid, polyimides, and alginates. It might also in some circumstances be suitable to use copolymer mixtures of the foregoing. The preferred polymers, however, are non-ionic or non-electrolyte hydrophilic polymers or copolymers such as PEO, PVP, PAAm, and HEC because these materials do not contain large numbers of ionizable moieties which would compete as charge carriers with the drug to be iontophoretically administered.

High molecular weight coagulant grade Polyox PEO typically has a weight of about 5 to 7 million Daltons, and has a high degree of linearity. It is nontoxic, relatively inert, and forms non-toxic degradation products. Because of its large molecular weight and high degree of linearity, hydrated PEO is viscous and quite cohesive. When introduced into the reticulum of a reticulated material, these properties prevent the PEO from being easily squeezed out of the pores of the reticulum, yet still allows fluidity which permits the PEO-loaded reticulated element to conform to minute skin features, such as skin crevices and around hair follicles.

Selection of a reticulated element having relatively small pore size assists in preventing loss of the PEO from the reticulum upon hydration, which is advantageous since loss of PEO from the reticulum could result in replacement by air bubbles, which would in turn disturb the lateral distribution of current in the reticulated element. Use of small pores also contributes to rapid hydration, probably due to wicking through capillary action.

Use of relatively small pores also works as a constraint against flow of hydrophilic polymer from the reticulum, even when substantial pressure is applied. This favorable characteristic permits electrodes incorporating these features to withstand substantial short-term compression.

In addition, the use of many small pores provides a very large surface area upon which to deposit hydrophilic polymer. This high surface area to volume ratio greatly enhances the rate of hydration of dried polymer.

A pore size corresponding to a pore density of about 100 pores per linear inch is currently preferred, although other pore sizes would be suitable depending upon factors such as the viscosity of the particular hydrophilic material utilized, anticipated compressions to which the electrode will be exposed, and the like. For most hydrophilic polymers, pore sizes in the range of about 60 to about 150 pores per linear inch are most suitable.

In situations where the electrode is to be stored in a non-hydrated form until use, it has been found useful to add a solution of Tween 20 nonionic surfactant (available from ICI America) to PEO prior to loading the reticulated element. The addition of a surfactant such as Tween 20 has been found to aid the rate of wetting during hydration. Although for purposes of brevity the following discussion is primarily directed to the use of Tween 20, it should be understood that other surfactants could also be used in place of Tween 20 in those situations where a surfactant is desired to be used. Examples of other useful surfactants are Neodol 91-6 (a nonionic primary alcohol ethoxylate manufactured by Shell Chemical Co.); Tergitol 15-S-7 (a nonionic secondary alcohol ethoxylate manufactured by Union Carbide); Pluronic Poloxamer F68 or F127 made by BASF; and Duponol C or Duponol XL (anionic sodium lauryl sulfates manufactured by Dupont Chemical Corp.). It is desirable that the surfactant be substantially nonionic, although small quantities of ionic moieties can be permitted.

A currently preferred ratio of PEO to Tween 20 is about 1 part PEO to about 1.15 parts Tween 20. The mixture of PEO and Tween 20 applied to a 100 ppi open cell polyurethane foam preferably comprises about 32 percent of the total dry weight of the reticulated element. It will be appreciated, however, that substantial variations in the ratio of PEO to Tween 20 and in the final percentage of the dry weight of the reticulated element can occur without departing from the inventive concepts disclosed and claimed herein.

Figure 5:
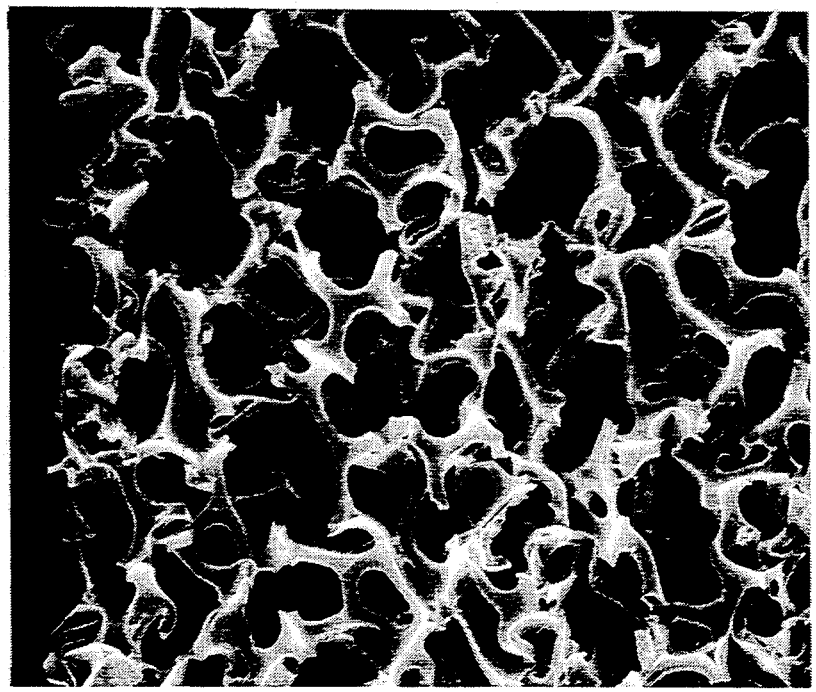
FIG. 5 is a photograph taken through a scanning electron microscope showing the reticulated element of FIG. 4 loaded with hydrogel for use in connection with the present invention.

In preparing the reticulated element, it is preferable to cover significant portions of the reticulum with PEO and Tween 20, while avoiding formation of skins or films which would tend to block the pores and hence would slow down the rate of hydration. FIG. 5 is a photomicrograph similar to that shown in FIG. 4, showing reticulum substantially loaded with PEO/Tween 20.

For example, several combinations of reticulated elements, hydrophilic polymer and surfactant have been investigated. Table 1 summarizes the results of these investigations:

TABLE 1

| Reticulated Material | Useful Combinations of Polymer and Surfactant (Stated as dry weight percentages in dry reticulated material) |
|---|---|
| Foamex Felted Z-90 Firmness 2 Polyurethane Foam | PEO: 10 to 20%, with 15% preferred Tween 20: 10 to 25%, with 17% preferred |
| Foamex Felted Z-90 | PEO: 5 to 30%, with 17% preferred Neodol 91-6: 1 to 10%, with 5% preferred |
| Crest Felted S-90Z Firmness 2 Polyurethane Foam | PEO: 10 to 20%, with 15% preferred Tween 20: 10 to 25%, with 17% preferred |
| Foamex Acquell | PEO: 10 to 40%, with 25% preferred |

TABLE 1-continued

| Reticulated Material | Useful Combinations of Polymer and Surfactant (Stated as dry weight percentages in dry reticulated material) |
| --- | --- |
| Foam, 90 ppi | Neodol 91-6: 1 to 10%, with 5% preferred |
| Rippey PVA Foam E-1 | PEO: 5 to 30%, with 15% preferred<br>Tween 20: 5 to 30%, with 17%% preferred |
| Matted Rayon Cosmetic Squares | PEO: 10 to 50%, with 25% preferred<br>Tween 20: 10 to 20%, with 15% preferred |

Presently preferred dimensions for the reticulated element of FIGS. 1 and 2 are about 2.5×4.5 centimeters, these being suitable for most typical iontophoretic applications. A presently preferred thickness for the reticulated element is about 2.5 millimeters, because this thickness is subject to rapid hydration, is adequate to hold a reasonable volume of drug solution, and provides a suitable physical barrier between the conductive element and the skin, thereby avoiding burns. Nevertheless, unlike conventional iontophoretic electrode designs, a reticulated element in accordance with the present invention may be constructed in a wide variety of shapes and sizes. Further, it may be easily cut, sewn, glued or welded into three-dimensional patterns suitable for placement around irregular surfaces such as knuckles, fingers, toes, elbows, or the like. It is readily conformable to desired shapes even when dry, making handling and manufacture much easier than prior materials, such as the stacks of crosslinked hydrogel sheets used heretofore. These properties make it possible to construct specialized electrode designs such as illustrated in copending patent application Ser. No. 07/608,565, filed Nov. 2, 1990, entitled "Apparatus For Treating and Preventing Infection of a Fingernail, Toenail, and the Like", which copending application is hereby incorporated in its entirety by reference.

Figure 3:
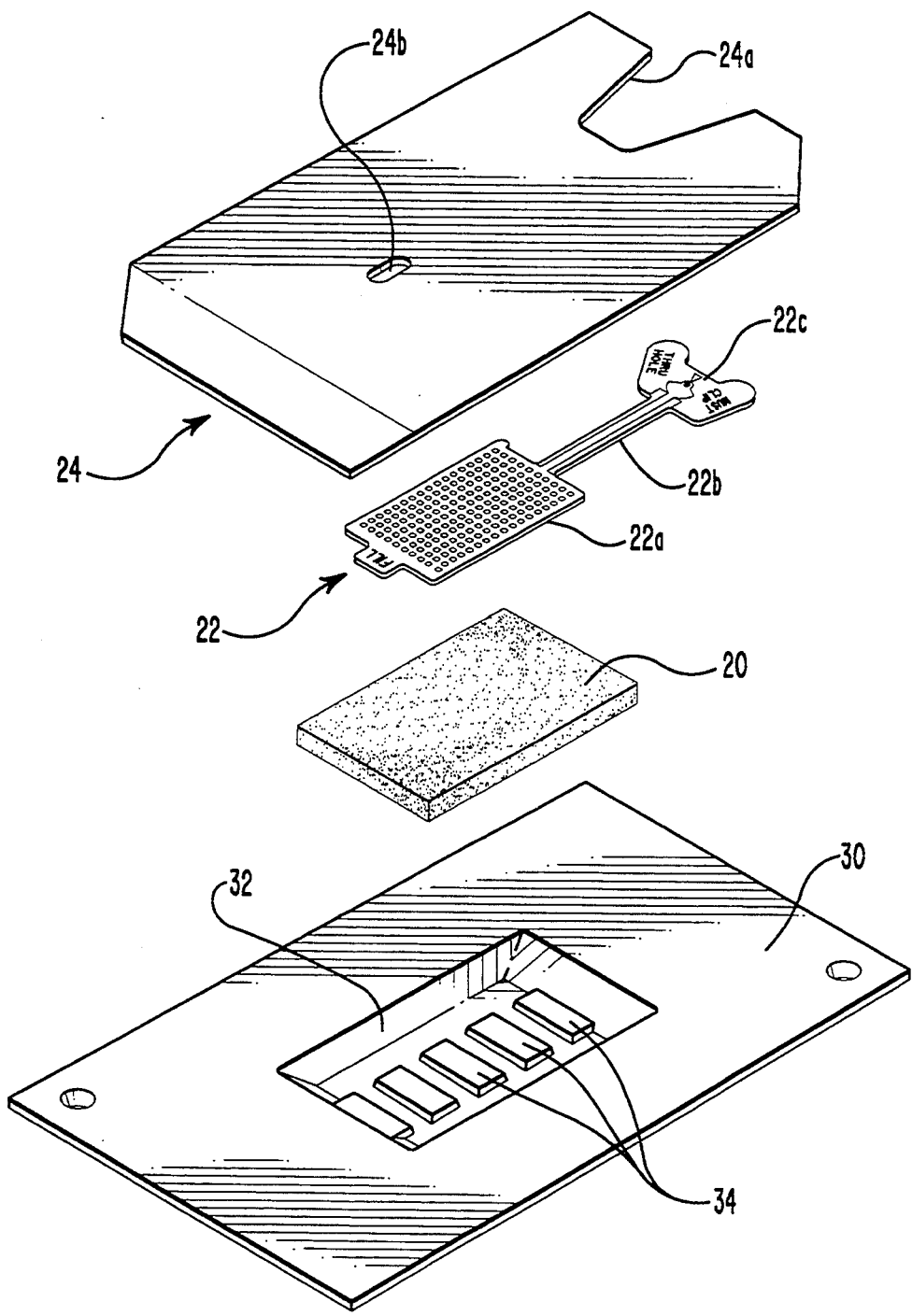
FIG. 3 is an exploded perspective view of the electrode of FIG. 1 together with a packaging element.

As better seen in FIG. 3, the main body 22a of the conductive element 22 is advantageously provided with an extension member 22b which extends from the electrode and is configured for attachment, such as at point 22c, to an electrical lead from an iontophoresis power source (not shown). Any suitable conductive element may be used, although it is presently preferred that it be formed by applying a silver-containing conductive ink to a flexible polymer material so that the conductive element is capable of conforming to gross alterations in the surface over which the electrode is applied. Preferably, such ink is applied in a pattern, such as best depicted in FIG. 3, in order to exercise control over current density across the face of the reticulated element. For example, in FIG. 3, it is illustrated that the ink pattern has a plurality of circular voids across the face thereof. Such voids may be formed so as to be smaller in size near the edges of the electrode and larger near the center (not specifically shown) in order to assist in establishing a uniform current density. It will be appreciated that other void shapes or patterns could be employed in order to control or establish a suitable distribution of current density.

FIGS. 1, 2 and 3 illustrate the use of an adhesive element 24 in association with the reticulated element and the conductive element. Adhesive element 24 is advantageously formed of a flexible polymer sheet 26 and an adhesive layer 28. In the embodiment shown in FIGS. 1 and 2, the significant overlap of adhesive element 24 beyond the edges of the reticulated element permits it to serve dual functions: (1) it serves as means for securing the reticulated element to the conductive element so that electric current will be distributed substantially uniformly through the reticulated element when hydrated and when current is delivered to the conductive element from an external electric current source; and (2) it serves to secure the electrode at a desired location on a patient so that it will not be inadvertently moved or dislodged. As best seen in FIGS. 1 and 3, it is useful to provide a cutout 24a at one side of adhesive element 24 so as to expose extension member 22b and attachment point 22c.

It is useful to further provide means for hydrating the reticulated element. FIG. 3 illustrates use of a reservoir element 30 which serves this function. Advantageously, reservoir element 30 is sized so as to be coextensive with or slightly larger than adhesive element 24. The adhesive element may be secured directly to reservoir element 30, the latter serving the function of a release liner. Tray member 32 is provided to form a recess for receiving the reticulated element, with extra space for receiving an aqueous solution of a drug solution. An access port 24b is formed through adhesive element 24 in order to permit introduction of the aqueous solution into tray member 32. The base of the tray member may be provided with a plurality of ridges 34 to assist in even distribution of the aqueous solution to the underside of the reticulated element.

In typical uses, the embodiment of FIGS. 1-3 is packaged until use, at which time a solution of drug(s) to be administered is introduced through access port 24b into tray member 32 so as to commence hydration of the reticulated element. After a suitable period, typically about 30 seconds, the electrode may be separated from reservoir element 30 and affixed at the desired location on the tissue of a patient (or animal) at the location where drug is to be administered. Upon hydration, the solution phase of the reticulated element has a very high water content, typically in excess of about 96 percent, and is exceedingly tacky and conformable to underlying tissue over which it is placed.

A second electrode, commonly referred to as a "dispersive" electrode, is secured at a nearby location, and both electrodes are connected to a power source. Iontophoresis is then conducted in the conventional manner. Although a Karaya gel electrode is typically used as the dispersive electrode, it should be understood that an electrode of the present invention could be used as the dispersive electrode.

Alternatively, drug may be dispersed together with PEO and Tween 20 throughout the reticulated element during the manufacturing process. In this case, hydration is performed using water or a suitable electrolyte solution without further addition of drug. Or, drugs which might cross-react if added together too soon might be combined by including one in the reticulated member and another in the hydrating solution. Another alternative is to hydrate the reticulated element with a suitable drug solution at the time of manufacture and to package the electrode with the reticulated element in the hydrated state so that it is ready to use without further treatment by the user. The embodiment of FIG. 3 would still be appropriate, omitting only the access port 24b which would be unnecessary and would otherwise permit the reticulated element to dry out. Other variations in use and construction will be readily apparent in light of the present disclosure.

Considerations when Loading PEO Into the Reticulum

In light of the fact that since one of the advantages of the apparatus of the present invention is the resistance of hydrophilic polymer to being squeezed from the pores of the reticulated element, it might be asked how the polymer is loaded into the reticulum in the first place. In fact, the small pore size and substantial thickness of the reticulated material used in connection with the typical apparatus of the present invention are significant obstacles to loading the reticulum with viscous hydrophilic polymers. By way of summary, the solution lies in use of appropriate solvents to render the polymer sufficiently fluid to permit it to be loaded into the reticulum and thereafter drying the reticulum so as to remove the solvents. The following discussion deals with the principal issues which ought to be controlled in order to obtain a consistently useful product.

Various properties of reticulated materials, hydrophilic polymers and surfactants can have an important effect upon the selection of appropriate combinations and appropriate manufacturing methods for use in preparing electrodes in accordance with the present invention.

For example, the effect on a reticulated material of wetting and its tolerance to solvents must be considered. Some reticulated materials have hydrophobic surfaces which require the use of hydrophobic solvent or surfactant mixes to enable a polymer solution to become affixed to the reticulum. Some materials will dissolve or become brittle after exposure to solvents.

Most reticulated materials become swollen, at least to some extent, when wetted. This can be beneficial, because swelling can aid the process of loading the reticulated material with polymer and surfactant by enlarging the pores, and thereby providing easier entry of the viscous polymer/surfactant solution. Yet, too much swelling can lead to a loss of dimensional stability when the reticulated element is dried after being loaded with polymer and surfactant. For example, felted foams (those which are compressed under heat and pressure), can become irreversibly "unfelted" when subjected to excess swelling.

The use of solvents is important in the manufacture of a loaded reticulated element, because they permit rapid loading of otherwise overly viscous polymers into small pores. Yet, the use of solvents can cause problems in the handling of polymer, as well as in the handling of the reticulated material.

For example, the simple act of mixing solvent with polymer can be difficult when dealing with high molecular weight, nonionic polymers. Further, the requirement to avoid shearing the polymers or permitting them to clump when wetted requires care in mixing. One useful method is to predisperse the polymer in a nonsolvent which is added to a miscible final solvent. Another method is to disperse the polymer in a cold solvent in which solubility is very low at low temperature, but high a higher temperature, followed by raising the temperature so as to solubilize the dispersed polymer. Yet another method is to use commercially available metering mixers which continuously and gravimetrically feed a small quantity of polymer into metered portions of an appropriate solvent.

Loading a solution of polymer into the reticulum of a reticulated element is directly affected by the ability of the solution to wet the surfaces of the reticulum and the viscoelasticity of the polymer solution. Appropriate selection of solvent(s) and surfactant(s) can improve wettability and viscoelasticity.

It is advantageous to select a polymer that is stable during a subsequent drying process. There is a tendency for drying polymer to shrink as it becomes dry; this can affect the dimensional stability of the dried reticulated element. Careful selection of polymer type, polymer molecular weight, additives, and quantity can largely control this problem.

It will be appreciated that several of the foregoing factors are affected by the solvent system selected. Selection of a solvent system depends to a significant degree on the mix method to be used, since the solvent must solubilize the polymer at the appropriate stage in the mixing process, and should achieve a viscosity conducive to effective loading.

Use of different solvents with the same percentage of polymer can result in solutions having dramatically different viscosities. For example, 1.3 percent coagulant grade Polyox PEO in trichloroethane has a viscosity of about 500 cps, while 1.3 percent Polyox in 10% isopropyl alcohol/water has a viscosity of about 5000 cps.

Conclusion

From the foregoing discussion, it is apparent that the present invention is a substantial improvement over previous designs. It provides for the manufacture of electrodes which are conformable to the contours of tissue into which a drug is to be administered while maintaining the capability of rapid and uniform hydration in those instances where a dry electrode is to be hydrated at the time of use. It is susceptible to a wide variety of shapes and sizes, including special configurations suitable for use with body parts such as fingers and toes. The high level of hydration, conformability, and tackiness contributes to exceedingly high efficiency with minimal electrode-induced unequal current distribution at different skin locations. Further, because of the relatively low cost of open cell polyurethane foam or other reticulated materials, and the ease of handling same, the present invention provides for manufacture of iontophoretic electrodes which are relatively easy to manufacture at reasonably low cost.

It will be appreciated that although the best mode presently contemplated for the construction of electrodes in accordance with the present invention have been disclosed, the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Patent is:

1. An electrode for use in the iontophoretic delivery of an ionic drug comprising:
    a conductive element for receiving an electric current delivered from an electric current source;
    a reticulated element including a reticulum structure and a plurality of pores formed by said reticulum structure for receiving an ionic drug solution at the time of iontophoretic delivery, said reticulated element comprising an open cell polyurethane foam having approximately 100 pores per linear inch;

a plurality of the reticulum structure of said reticulated element having applied thereto high molecular weight polyethylene oxide and surfactant; and means for securing the reticulated element to the conductive element so that electric current will be distributed substantially uniformly through the reticulated element when hydrated and when current is delivered to the conductive element from an electric current source.

2. An electrode as defined in claim 1 further comprising means for rehydrating the reticulated element.

3. An electrode as defined in claim 2, wherein the means for rehydrating the reticulated element comprises a reservoir element for receiving the reticulated element and a solution for hydrating same.

4. An electrode as defined in claim 1 wherein the polyurethane foam of the reticulated element is substantially dry, and hence must be hydrated prior to use in administering drug.

5. An electrode as defined in claim 4, wherein a solution including drug is used to hydrate the reticulated element prior to use.

6. An electrode as defined in claim 4, wherein an ionic form of a drug is dispersed in the dry reticulated element.

7. An electrode as defined in claim 1, wherein the polyethylene oxide comprises in the range of about 10 to about 20 percent of the dry weight of the reticulated element, and the surfactant comprises in the range of about 10 to about 25 percent of the dry weight of the reticulated element.

8. An electrode as defined in claim 1, wherein the polyethylene oxide comprises about 15 percent of the dry weight of the reticulated element, and the surfactant comprises about 17 percent of the dry weight of the reticulated element.

9. An electrode as defined in claim 1, wherein the polyurethane foam of the reticulated element is substantially hydrated with an ionic drug solution so that said electrode need not be hydrated prior to use.

10. An electrode as defined in claim 1, wherein the reticulated element is approximately 2.5 millimeters thick.

11. An electrode as defined in claim 1, wherein the pore size of the reticulated element is in the range of about 60 to about 150 pores per linear inch.

12. An electrode as defined in claim 1, wherein the conductive element comprises a conductive pattern to establish a uniform current density across the face thereof.

* * * * *